US00PP29759P2

(12) United States Plant Patent
Klemm et al.

(10) Patent No.: US PP29,759 P2
(45) Date of Patent: Oct. 16, 2018

(54) ***CALIBRACHOA* PLANT NAMED 'KLECA16320'**

(50) Latin Name: ***Calibrachoa* sp.**
Varietal Denomination: KLECA16320

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/731,872

(22) Filed: Aug. 16, 2017

(30) Foreign Application Priority Data

Mar. 21, 2017 (QZ) ..... PBR 2017/0699

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ..... A01H 5/02
See application file for complete search history.

(56) References Cited

PUBLICATIONS http://www.ball.com.br/wp-content/uploads/2016/11/Ball-Seed-New-Varieties-2017.pdf; 2016; 1 page.*
https://www.ballseed.com/PlantInfo/?phid=066007160000687; 2018; 3 pages.*
https://www.bfgsupply.com/_CE/pagecontent/Documents/Plant%20Connection/Gro%27n%20Sell%20Annuals.pdf; 2016-2017; 1 page.*

* cited by examiner

*Primary Examiner* — Kent L Bell
(74) *Attorney, Agent, or Firm* — Barbara Campbell; Cochran Freund & Young LLC

(57) ABSTRACT

A new *Calibrachoa* plant particularly distinguished by having purple flowers and a semi-trailing and mounding habit, is disclosed.

1 Drawing Sheet

Genus and species: *Calibrachoa* sp.
Variety denomination: 'KLECA16320'.

CROSS-REFERENCE TO RELATED APPLICATIONS

This application claims priority to and the benefit of European Community Plant Variety Rights application filed on Mar. 21, 2017, File No. 2017/0699, the entire contents of which are incorporated herein by reference for all purposes.

BACKGROUND OF THE NEW PLANT

The present invention comprises a new and distinct variety of *Calibrachoa*, botanically known as *Calibrachoa* sp., and hereinafter referred to by the variety name 'KLECA16320'. 'KLECA16320' originated from a controlled-cross performed in summer 2012 between two unpatented *Calibrachoa* plants, the proprietary female *Calibrachoa* parent 'CA-2011-0565' and the proprietary male *Calibrachoa* parent 'CA-2011-0546', in Stuttgart, Germany.

The seeds from the cross were sown and plants were grown in a greenhouse for evaluation, where an individual plant designated 'KLECA16320' was selected from the group of plants May 2013 in Stuttgart, Germany. In May 2013, 'KLECA16320' was first vegetatively propagated by terminal tip cuttings. 'KLECA16320' was found to reproduce true to type in successive generations of asexual propagation via tissue culture and terminal tip cuttings.

SUMMARY

The following are the most outstanding and distinguishing characteristics of this new variety when grown under normal horticultural practices in Stuttgart, Germany.

1. Purple flowers; and
2. A semi-trailing and mounding habit.

DESCRIPTION OF THE PHOTOGRAPH

This new *Calibrachoa* plant is illustrated by the accompanying photograph which shows the whole plant, including the habit, the foliage, the flowers, and the buds. The photograph is of an 8-week-old plant grown in a pot outdoors in Stuttgart, Germany in May 2014. The colors shown are as true as can be reasonably obtained by conventional photographic procedures.

DESCRIPTION OF THE NEW VARIETY

The following detailed descriptions set forth the distinctive characteristics of 'KLECA16320'. The data which define these characteristics were collected from asexual reproductions carried out in Stuttgart, Germany. Data was collected on 20-week-old plants grown in an outdoor field in Stuttgart, Germany. Color references are to The R.H.S. Colour Chart of The Royal Horticultural Society of London (R.H.S.) (2007).

Classification:

*Family*.—Solanaceae.
*Botanical*.—*Calibrachoa* sp.

*Common.*—*Calibrachoa.*
*Designation.*—'KLECA16320'.

Parentage:
*Female parent.*—Proprietary *Calibrachoa* line 'CA-2011-0565' (unpatented).
*Male parent.*—Proprietary *Calibrachoa* line 'CA-2011-0546' (unpatented).

Plant:
*Life cycle.*—Annual.
*Habit.*—Semi-trailing and mounding.
*Height (from soil line to top of foliage).*—10.0 cm.
*Spread.*—48.0 cm.
*Propagation.*—Vegetatively propagated by tip cuttings and tissue culture.
*Time to produce a rooted cutting.*—3 weeks.

Stems:
*Stem color.*—RHS 145A.
*Pubescence.*—Absent.
*Diameter.*—0.2 cm to 0.3 cm.
*Length.*—13.0 cm. From soil line to first node: 2.0 cm. Total length: 23.0 cm.
*Internode length.*—2.0 cm to 3.0 cm.

Leaves:
*Arrangement.*—Opposite.
*Shape.*—Narrow lanceolate.
*Apex.*—Broadly acute.
*Base.*—Attenuate.
*Margin.*—Ciliate.
*Surface texture.*—Smooth.
*Surface pubescence.*—Absent.
*Pubescence color.*—Absent.
*Venation pattern.*—Arcuate.
*Venation color.*—Upper surface: RHS 144C. Lower surface: RHS 144D.
*Length.*—2.3 cm.
*Width.*—0.6 cm.
*Color.*—Upper surface: RHS 137B. Lower surface: RHS 138B.
*Fragrance.*—Absent.

Flowers:
*Flower type.*—Determinate inflorescence with single flowers.
*Flowering requirements.*—A minimum of light sun is required.
*Duration of flowers on the plant.*—6 days.
*Shape.*—Funnel-form.
*Fragrance.*—Absent.
*Flower depth.*—2.3 cm.
*Flower tube length.*—1.6 cm.
*Flower tube diameter.*—0.6 cm.
*Flower diameter.*—3.5 cm.
*Pedicel color.*—RHS 145B.
*Pedicel length.*—1.5 cm.
*Pedicel diameter.*—0.1 cm.

Flower buds:
*Surface texture.*—Smooth.
*Length.*—1.6 cm.
*Diameter.*—0.3 cm.
*Shape.*—Irregular to oblong.
*Color.*—RHS 86C.

Peduncle:
*Length.*—0.6 cm.
*Diameter.*—0.1 cm.
*Color.*—RHS 145A.
*Surface texture.*—Smooth.
*Anthocyanin color.*—RHS N200A.

Petals:
*Shape.*—Obcordate.
*Length.*—1.6 cm.
*Apex.*—Truncate.
*Margin.*—Entire, with medium undulation.
*Base.*—Open and fused in the tube.
*Pubescence.*—Absent.
*Lobe length.*—1.6 cm.
*Lobe width.*—1.7 cm.
*Color.*—Lobe color: Upper surface: RHS 90C for mature flowers and RHS 86A for immature flowers. Lower surface: RHS 86D for mature flowers and RHS 86C for immature flowers. Corolla tube color: Inner surface: RHS 14C. Outer surface: RHS 13D.
*Fragrance.*—Absent.

Sepals:
*Calyx.*—Funnel-shaped.
*Shape.*—Lanceolate.
*Apex.*—Acute.
*Margin.*—Entire.
*Length.*—1.2 cm.
*Diameter.*—0.4 cm.
*Color.*—Upper surface: RHS 143A. Lower surface: RHS 143C.

Reproductive organs:
*Stamen.*—Quantity per flower: 5. Anther color: RHS 7A. Filament color: RHS 145C. Filament length: 0.9 cm. Pollen color: RHS 7A. Pollen amount: Medium.
*Pistil.*—Ovary, placenta arrangement: Ovate. Pistil number per flower: 1. Pistil length: 1.0 cm. Stigma color: RHS 143B. Style length: 0.8 cm. Style color: RHS 150C.

Fruit and seed set: Not observed.

COMPARISON WITH PARENTAL LINES AND KNOWN VARIETY

'KLECA16320' is distinguished from the parental lines as described in Table 1.

TABLE 1

Comparison with Parental Lines

| Characteristic | 'KLECA16320' | Female parent 'CA-2011-0565' | Male Parent 'CA-2011-0546' |
|---|---|---|---|
| Flower color, mature, upper surface | RHS 90C | RHS N88C | RHS N87D |

'KLECA16320' is most similar to the commercial *Calibrachoa* plant named 'KLECA12236' (U.S. Plant Pat. No. 25,887). Differences between the two varieties are described in Table 2.

TABLE 2

Comparison with Similar Variety

| Characteristic | 'KLECA16320' | 'KLECA12236' |
|---|---|---|
| Flower color, mature, upper surface | RHS 90C | RHS N87A |

We claim:

1. A new and distinct variety of *Calibrachoa* plant named 'KLECA16320' as illustrated and described herein.

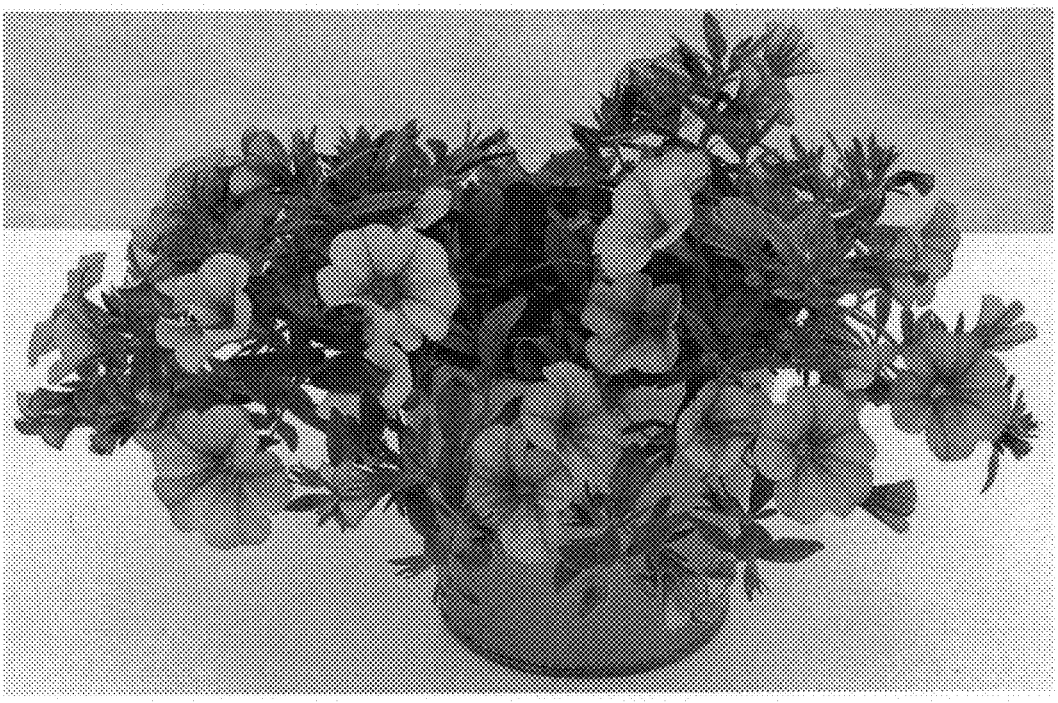

* * * * *